(12) United States Patent
Han et al.

(10) Patent No.: US 6,949,667 B2
(45) Date of Patent: Sep. 27, 2005

(54) ALKENYLPHOSPHONIC ESTER AND PREPARATION PROCESS THEREOF

(75) Inventors: Li-Biao Han, Tsukuba (JP); ChangQiu Zhao, Tsukuba (JP); Masato Tanaka, Tsukuba (JP)

(73) Assignee: National Institute of Advanced Industrial Science and Technology (JP)

(*) Notice: Subject to any disclaimer, the term of this patent is extended or adjusted under 35 U.S.C. 154(b) by 60 days.

(21) Appl. No.: 10/220,067

(22) PCT Filed: Dec. 28, 2000

(86) PCT No.: PCT/JP00/09412

§ 371 (c)(1),
(2), (4) Date: Dec. 4, 2002

(87) PCT Pub. No.: WO01/64694

PCT Pub. Date: Sep. 7, 2001

(65) Prior Publication Data

US 2003/0166612 A1 Sep. 4, 2003

(30) Foreign Application Priority Data

Mar. 2, 2000 (JP) .......................... 2000-057610
Nov. 24, 2000 (JP) .......................... 2000-357348

(51) Int. Cl.⁷ .............................................. C07F 9/40
(52) U.S. Cl. ..................... 558/87; 558/73; 558/89; 558/117
(58) Field of Search ............................. 558/73, 87, 89, 558/117

(56) References Cited

U.S. PATENT DOCUMENTS 3,629,367 A 12/1971 DeMott et al. ............. 260/867
5,109,033 A 4/1992 Grey et al. ................. 521/147

OTHER PUBLICATIONS

Manouni et al (1989):STN International CAPULS database (Columbus, Ohio), Accession No. 1990: 77355.*
Li–Biao Han and Masato Tanaka (1996): J. Am. Chem. Soc. vol. 118, pp. 1571–1572.*
Chemical Abstracts, 64:15916b.
Phosphorous and Sulfur, 1983, vol. 16, pp. 345–360 (1983).
Ogranometallics 2000, 19, 4196–4196.
Phosphorus and Sulfur, 1983, vol. 16, pp. 345–360, Kutyrev et al.

* cited by examiner

*Primary Examiner*—Golam M M Shameem
(74) *Attorney, Agent, or Firm*—Lorusso, Loud & Kelly

(57) ABSTRACT

Novel alkenylphosphonic acid esters of the following general formula (I):

$$R^1CH=CR^2[P(O)(OCR^3R^4CR^5R^6O)] \qquad (I)$$

and a simple process for the preparation thereof are provided by the use of secondary cyclic phosphonic acid esters as the starting material.

15 Claims, No Drawings

ALKENYLPHOSPHONIC ESTER AND PREPARATION PROCESS THEREOF

This application is a 371 of PCT/JP00/09412 Dec. 28, 2000, which claims the benefit of foreign priority under 35 U.S.C. § 119(a)–(d) to Japan 2000-057610 Mar. 2, 2000 and Japan 2000-357348 Nov. 24, 2000.

TECHNICAL FIELD

This invention relates to a novel alkenylphosphonic acid ester and to a process for the preparation thereof.

BACKGROUND ART

Alkenylphosphonic acid esters have a basic skeleton found in natural products and are known to exhibit physiological activity by interaction with an enzyme. Alkenylphosphonic acid esters may also be used as a raw material for performing Horner-Emmons addition reaction with a carbonyl compound and, therefore, are widely used for the synthesis of olefins.

A method is generally known to produce an alkenylphosphonic acid ester with the formation of carbon-phosphorus bond, in which the corresponding halide is subjected to substitution with a dialkylphosphite. This method requires the addition of a base for capturing hydrogen halide produced as the reaction proceeds. Thus, a large amount of a hydrogen halide salt is produced as by-product. In addition, the unsaturated halogen compound used as the starting material is not industrially easily feasible and is toxic in nature. Therefore, the above method is not advantageous from the industrial point of view.

Recently, a method was found in which a non-cyclic secondary phosphonic acid ester is added to an acetylene compound in the presence of a palladium catalyst (Journal of American Chemical Society, vol. 118, p. 1571 (1996); Japanese patent No. 2775426). The selectivity attained by this method is low. Further, the phosphonic acid ester compound, the major product of this method, is non-cyclic. In the reaction with the terminal acetylene group, the phosphorus is bonded to the carbon atom located on an inner side from the terminal carbon of the carbon-carbon unsaturated bond to give an α-addition product rather than β-addition product in which the phosphorus is added to the terminal carbon.

The present invention is aimed at the provision of a novel alkenylphosphonic acid ester and a simple process for the preparation thereof by the use of secondary cyclic phosphonic acid ester as the starting material.

DISCLOSURE OF THE INVENTION

The present inventors have made an earnest study on reactions of easily feasible secondary cyclic phosphonic acid esters with acetylene compounds and have found that the addition reaction proceeds in the presence of a specific catalyst and gives novel alkenylphosphonic acid esters with high yield and selectivity. The present invention is based on the above finding.

In accordance with the present invention there are provided the following methods:

(1) An alkenylphosphonic acid ester compound of the following general formula (I):

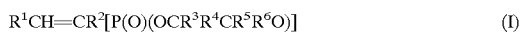

wherein $R^1$ and $R^2$ each stand for a hydrogen atom, an alkyl group, a cycloalkyl group, an aryl group, an aralkyl group, a heteroaryl group, an alkenyl group, an alkoxy group, an aryloxy group or a silyl group, provided that $R^1$ does not stand for a hydrogen atom or a methyl group and $R^3$, $R^4$, $R^5$ and $R^6$ each stand for a hydrogen atom, an alkyl group, a cycloalkyl group, an aralkyl group or an aryl group.

(2) A process for the preparation of an alkenylphosphonic acid ester compound, comprising reacting an acetylene compound of the following formula (II):

group, a cycloalkyl group, an aryl group, an aralkyl group, a heteroaryl group, an alkenyl group, an alkoxy group, an aryloxy group or a silyl group, provided that $R^1$ does not stand for a hydrogen atom or a methyl group, with a cyclic secondary phosphonic acid ester of the following formula (III):

wherein $R^3$, $R^4$, $R^5$ and $R^6$ each stand for a hydrogen atom, an alkyl group, a cycloalkyl group, an aralkyl group or an aryl group, in the presence of a catalyst of a metal of Group 9 of the Periodic Table, preferably a rhodium catalyst, to obtain an alkenylphosphonic acid ester compound of the following formula (I):

wherein $R^1$, $R^2$, $R^3$, $R^4$, $R^5$ and $R^6$ have the same meaning as above.

(3) A process for the preparation of an alkenylphosphonic acid ester compound as recited in (2) above, characterized in that a polar solvent is used.

(4) An alkenyldiphosphonic acid ester compound of the following general formula (IV):

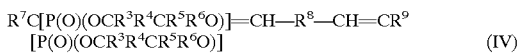

wherein $R^3$, $R^4$, $R^5$ and $R^6$ have the same meaning as above, $R^7$ and $R^9$ each stand for a hydrogen atom, an alkyl group, a cycloalkyl group, an aryl group, an aralkyl group, a heteroaryl group, an alkenyl group, an alkoxy group, an aryloxy group or a silyl group and $R^8$ stands for an alkylene group, a cycloalkylene group or an arylene group.

(5) An alkenyldiphosphonic acid ester compound of the following general formula (V):

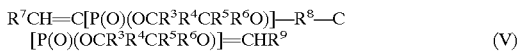

wherein $R^3$, $R^4$, $R^5$, $R^6$, $R^7$ and $R^8$ have the same meaning as above.

(6) A process for the preparation of an alkenyldiphosphonic acid ester, comprising reacting a diacetylene compound of the following formula (VI):

wherein $R^7$, $R^8$ and $R^9$ have the same meaning as above, with a cyclic secondary phosphonic acid ester of the following formula (III):

wherein $R^3$, $R^4$ and $R^5$ and $R^6$ have the same meaning as above, in the presence of a catalyst of a metal of Group 9 of the Periodic Table, preferably a rhodium catalyst, to obtain an alkenyldiphosphonic acid ester of the following formula (IV) and/or formula (V):

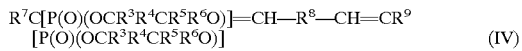

wherein $R^3$, $R^4$, $R^5$, $R^6$, $R^7$, $R^8$ and $R^9$ have the same meaning as above.

(7) A process for the preparation of an alkenyldiphosphonic acid ester compound as recited in (6) above, characterized in that a polar solvent is used.

The alkenylphosphonic acid ester represented by the above general formula (I) and the alkenyldiphosphonic acid esters represented by the above general formulas (IV) and (V) are novel compounds with a cyclic phosphonic acid ester structure which are not described in any literature. The novel compounds are useful as an agent for forming carbon-carbon bonds, for example, as an intermediate compounds for the production of physiologically active substances of medicaments or agricultural chemicals. Because of the cyclic structure, the novel compounds have considerably higher reaction activity (e.g. conversion into phosphonic acid by hydrolysis) as compared with similar non-cyclic compounds. Thus, the cyclic alkenylphosphonic acid ester is expected to allow chemical conversion, which would otherwise be difficult or impossible to perform, to proceed efficiently under milder conditions.

The alkenylphosphonic acid ester compound represented by the above general formula (I) may be easily produced by reacting an acetylene compound of the above formula (II) with a cyclic secondary phosphonic acid ester of the above formula (III) in the presence of a catalyst of a metal of Group 9 of the Periodic Table.

The acetylene compound used as a reaction raw material in the present invention is represented by the above formula (II) in which $R^1$ and $R^2$ each stand for a hydrogen atom, an alkyl group, a cycloalkyl group, an aryl group, an aralkyl group, a heteroaryl group, an alkenyl group, an alkoxy group, an aryloxy group or a silyl group.

When $R^2$ is a hydrogen atom and $R^1$ is a group other than a hydrogen atom, the acetylene compound of the above general formula (II) is an acetylene-terminated compound which gives, upon reaction with a cyclic secondary phosphonic acid ester of the above general formula (III), a β-addition product of an alkenylphosphonic acid ester compound of the above general formula (I).

The alkyl group has 1–18 carbon atoms, preferably 1–10 carbon atoms. Specific examples of the alkyl group include methyl, ethyl, propyl, hexyl and decyl.

The cycloalkyl group has 5–18 carbon atoms, preferably 5–10 carbon atoms. Specific examples of the cycloalkyl group include cyclohexyl, cyclooctyl and cyclododecyl.

The aryl group has 6–14 carbon atoms, preferably 6–10 carbon atoms. Specific examples of the aryl group include phenyl, naphthyl and substituted phenyl and naphthyl (e.g. tolyl, xylyl and benzylphenyl).

The heteroaryl groups are various heteroaromatic ring groups containing heteroatoms such as oxygen, nitrogen or sulfur and have 4–12 carbon atoms, preferably 4–8 carbon atoms. Specific examples of the heteroaryl group include thienyl, furyl, pyridyl and pyrrolyl.

The aralkyl group has 7–13 carbon atoms, preferably 7–9 carbon atoms. Specific examples of the aralkyl group include benzyl, phenethyl, phenylbenzyl and naphthylmethyl.

The alkenyl group has 2–18 carbon atoms, preferably 2–10 carbon atoms. Specific examples of the alkenyl group include vinyl and 3-butenyl.

The alkoxy group has 1–8 carbon atoms, preferably 1–4 carbon atoms. Specific examples of the alkoxy group include methoxy, ethoxy and buthoxy.

The aryloxy group has 6–14 carbon atoms, preferably 6–10 carbon atoms. Specific examples of the aryloxy group include phenoxy and napthoxy.

The silyl groups may include those which substituents such as alkyl, aryl, aralkyl and alkoxy. Specific examples of the silyl group include trimethylsilyl, triethylsilyl, triphenylsilyl, phenyldimethylsilyl and trimethoxysilyl.

The group $R^1$ and $R^2$ may contain a substituent inert to the reaction such as methoxy, methoxycarbonyl, cyano, dimethylamino, fluorine, chlorine or hydroxyl.

Illustrative of acetylene compounds suitably used in the present invention are non-substituted acetylene, butyne, octyne, phenylacetylene, trimethylsilylacetylene, ethynylthiophene, hexynenitrile and cyclohexenylacetylene. The present invention is not limited to these acetylene compounds.

The cyclic secondary phosphonic acid ester used as a reaction raw material in the present invention is represented by the above general formula (III) in which $R^3$, $R^4$, $R^5$ and $R^6$ each stand for a hydrogen atom, an alkyl group, a cycloalkyl group, an aralkyl group or an aryl group.

The alkyl group has 1–6 carbon atoms, preferably 1–4 carbon atoms. Specific examples of the alkyl group include methyl, ethyl, propyl and hexyl.

The cycloalkyl group has 3–12 carbon atoms, preferably 5–6 carbon atoms. Specific examples of the cycloalkyl group include cyclohexyl, cyclooctyl and cyclododecyl.

The aralkyl group has 7–13 carbon atoms, preferably 7–9 carbon atoms. Specific examples of the aralkyl group include benzyl, phenethyl, phenylbenzyl and naphthylmethyl.

The aryl group has 6–14 carbon atoms, preferably 6–10 carbon atoms. Specific examples of the aryl group include phenyl, naphthyl and substituted phenyl and naphthyl (e.g. tolyl, xylyl and benzylphenyl).

The alkenyldiphosphonic acid ester compound represented by the above general formulas (IV) and (V) may be easily produced by reacting a diacetylene compound of the above formula (VI) with a cyclic secondary phosphonic acid ester of the above formula (III) in the presence of a catalyst of a metal of Group 9 of the Periodic Table. The diacetylene compound used as a reaction raw material in the present invention is represented by the above formula (VI) in which $R^7$ and $R^9$ each stand for a hydrogen atom, an alkyl group, a cycloalkyl group, an aryl group, an aralkyl group, a heteroaryl group, an alkenyl group, an alkoxy group, an aryloxy group or a silyl group and $R^8$ stands for an alkylene group, a cycloalkylene group or an arylene group.

The alkyl group has 1–18 carbon atoms, preferably 1–10 carbon atoms. Specific examples of the alkyl group include methyl, ethyl, propyl, hexyl and decyl.

The cycloalkyl group has 5–18 carbon atoms, preferably 5–10 carbon atoms. Specific examples of the cycloalkyl group include cyclohexyl, cyclooctyl and cyclododecyl.

The aryl group has 6–14 carbon atoms, preferably 6–10 carbon atoms. Specific examples of the aryl group include phenyl, naphthyl and substituted phenyl and naphthyl (e.g. tolyl, xylyl and benzylphenyl).

The heteroaryl groups are various heteroaromatic ring groups containing heteroatoms such as oxygen, nitrogen or sulfur and have 4–12 carbon atoms, preferably 4–8 carbon atoms. Specific examples of the heteroaryl group include thienyl, furyl, pyridyl and pyrrolyl.

The aralkyl group has 7–13 carbon atoms, preferably 7–9 carbon atoms. Specific examples of the aralkyl group include benzyl, phenethyl, phenylbenzyl and naphthylmethyl.

The alkenyl group has 2–18 carbon atoms, preferably 2–10 carbon atoms. Specific examples of the alkenyl group include vinyl and 3-butenyl.

The alkoxy group has 1–8 carbon atoms, preferably 1–4 carbon atoms. Specific examples of the alkoxy group include methoxy, ethoxy and buthoxy.

The aryloxy group has 6–14 carbon atoms, preferably 6–10 carbon atoms. Specific examples of the aryloxy group include phenoxy and napthoxy.

The silyl groups may include those which substituents such as alkyl, aryl, aralkyl and alkoxy. Specific examples of the silyl group include trimethylsilyl, triethylsilyl, triphenylsilyl, phenyldimethylsilyl and trimethoxysilyl.

The alkylene group has 1–20 carbon atoms, preferably 1–10 carbon atoms. Specific examples of the alkylene group include methylene and tetramethylene.

The cycloalkylene group has 5–18 carbon atoms, preferably 5–10 carbon atoms. Specific examples of the cycloalkylene group include cyclopentylene and cyclohexylene.

The arylene group has 6–30 carbon atoms, preferably 6–14 carbon atoms. Specific examples of the arylene group include phenylene and nepthylene.

Illustrative of suitable diacetylene compounds 1,4-pentadiyne, 1,8-nonadiyne and diethynylbenzene. The present invention is not limited to these acetylene compounds.

For the purpose of efficiently performing the reaction in the present invention a catalyst of a metal belonging to the Group 9 of the Periodic Table, such as a metal catalyst of cobalt, rhodium or iridium is preferably used. Particularly a rhodium catalyst is preferred.

These catalyst may have various structures. Low valency catalysts may be suitably used. Monovalent catalysts having a tertiary phosphine or a tertiary phosphite as a ligand are especially suitably used. A precursor substance which can form in situ a low valency catalyst during reaction may also be suitably used.

A further suitable embodiment is a method in which a complex which does not contain a tertiary phosphine or a tertiary phosphite as a ligand is mixed with a tertiary phosphine or a tertiary phosphite during the reaction to form a low valency complex having a tertiary phosphine or a tertiary phosphite as a ligand. Various tertiary phosphines and tertiary phosphites may be used as the ligands exhibiting advantageous properties in any of the above methods. However, those tertiary phosphines and tertiary phosphites which has extremely strong electron donating properties are not always advantageous with respect to the reaction rate.

Examples of suitable ligands include triphenylphosphine, diphenylmethylphosphine, phenyldimethylphosphine, 1,4-bis(diphenylphosphino)butane, 1,3-bis(diphenylphosphino) propane, 1,2-bis(diphenylphosphino)ethane, 1,1'-bis (diphenylphosphino)ferocene, trimethylphosphite and triphenylphosphite. Illustrative of suitable complexes which do not contain a tertiary phosphine or a tertiary phosphite as a ligand and which are used in conjunction with the above-described ligands are acetylacetonatebis(ethylene)rhodium, chlorobis(ethylene)rhodium dimer, dicarbonyl (acetylacetonato)rhodium, hexarhodiumhexadecacarbonyl, chloro(1,5-cyclooctadiene)rhodium and chloro (norbornadiene)rhodium. The present invention is not limited to the above complexes. Illustrative of suitable phosphine or phosphite complexes are chlorocarbonylbis (triphenylphosphine)rhodium, hydridocarbonyltris (triphenylphosphine)rhodium, chlorotris (triphenylphosphine)rhodium and chlorocarbonylbis (trimethylphosphite)rhodium.

The complex catalyst is used in a catalytically effective amount and, generally, in an amount of up to 20 mole %, based on the acetylene compound. The acetylene compound and the disubstituted cyclic phosphonic acid ester are generally used in a molar ratio of 1:1. However, the use of a greater or smaller amount does not adversely affect the occurrence of the reaction.

The reaction may be carried out without using a solvent but may be performed using a solvent if necessary. Various solvents may be used. Examples of the solvent include hydrocarbons, halogenated hydrocarbons, ethers, ketones, nitrites and esters. These solvents may be used singly or as a mixture of two or more thereof. Above all, a polar solvent, especially a polar solvent having a dielectric constant of at least 3.5, such as acetone, tetrahydrofuran, acetonitrile or diethyl ether, is preferably used in the present invention.

With regard to a reaction temperature, too low a temperature fails to proceed the reaction at an advantageous rate, but too high a temperature may cause decomposition of the catalyst. Thus, the reaction temperature is generally selected from a range between minus 20° C. and 300° C., preferably between room temperature and 150° C.

Since the catalyst used in the above reaction is sensitive to oxygen, it is preferred that the reaction be carried out in an atmosphere of an inert gas such as nitrogen, argon or methane. The product may be easily separated from the reaction mixture by chromatography, distillation or recrystallization.

EXAMPLES

The present invention will be next described in more detail by examples but is not limited thereto.

Example 1

To 1 ml of toluene were added 1 mmol of $HP(O)(OCMe_2-CMe_2O)$, 1 mmol of phenylacetylene and 1.5 mol % of $RhCl(PPh_3)_3$ as a catalyst, and the mixture was reacted at 100° C. for 1 hour in an atmosphere of nitrogen. The reaction mixture was concentrated and separated by liquid chromatography to isolate 2-[(E)-2-phenylethenyl]-4.4.5.5-tetramethyl-1,3,2-dioxaphospholan-2-oxide with a yield of 96%. This compound is a novel substance not described in the literature and has the following spectral data.

$^1$H-NMR (500 MHz, $CDCl_3$): δ 7.61 (dd, 1H, J=17.3 Hz, $J_{hp}$=23.7 Hz), 7.35–7.49 (m, 5H), 6.13 (dd, 1H, J=17.3 Hz, $J_{HP}$=20.1 Hz), 1.52 (s, 6H), 1.40 (s, 6H); $^{13}$C-NMR (125.4 MHz, $CDCl_3$): δ 150.7, 134.8, 128.9, 127.9, 114.6 ($J_{CP}$= 188.3 Hz), 88.2, 24.7 ($J_{CP}$=3.1 Hz) 24.2 ($J_{CP}$=5.2 Hz) $^{31}$P-NMR (201.9 MHz, $CDCl_3$): δ 30.1 IR (KBr): 3005, 1640, 1490, 1460, 1392, 1263, 1151, 963, 932, 882, 800, 732 cm$^{-1}$ HRMS as $C_{14}H_{19}O_3P$: calculated: 266.1072. measured: 266.1092.

| Elementary analysis: | | |
| --- | --- | --- |
| calculated: | C, 63.15; | H, 7.19 |
| measured: | C, 63.48; | H, 7.27 |

Example 2

To 1 ml of toluene were added 1 mmol of $HP(O)(OCMe_2-CMe_2O)$, 1 mmol of phenylacetylene and a mixture of $[RhCl(cod)_2]$ (cod =1,5-cyclooctadiene) with $Ph_3P$ as a catalyst (2 mol % based on rhodium atom, Rh/P molar ratio=1/

2), and the mixture was reacted at 80° C. for 2 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 95%.

Example 3

Example 2 was repeated in the same manner as described except that the reaction was performed at room temperature. 20 Hours after start of the reaction, 2-[(E)-2-phenylethenyl]-4,4,5,5-tetramethyl-1,3,2-dioxaphospholan-2-oxide was obtained with a yield of 32%.

Example 4

Example 3 was repeated in the same manner as described except that a mixture of [RhCl(cod)$_2$](cod=1,5-cyclooctadiene) with Ph$_3$P (2 mol % based on rhodium atom, Rh/P molar ratio=1/1) was used as a catalyst. 20 Hours after start of the reaction, 2-[(E)-2-phenylethenyl]-4,4,5,5-tetramethyl-1,3,2-dioxaphospholan-2-oxide was obtained with a yield of 65%.

Examples 5–15

Example 1 was repeated in the same manner as described using various acetylene compounds to obtain phosphonic acid esters of the present invention. The results are summarized in Table 1.

TABLE 1

| Example | Acetylene | Product* | Yield (%) |
| --- | --- | --- | --- |
| 5 | n-C$_6$H$_{13}$—≡ | n-C$_6$H$_{13}$\\=/P(O)(OR)$_2$ | 97 |
| 6 | t-Bu—≡ | t-Bu\\=/P(O)(OR)$_2$ | 92 |
| 7 | Cl\\/\\≡ | Cl\\/\\/\\=/P(O)(OR)$_2$ | 96 |
| 8 | NC\\/\\≡ | NC\\/\\/\\=/P(O)(OR)$_2$ | 91 |
| 9 | HO–C(CH$_3$)$_2$–≡ | HO–C(CH$_3$)$_2$–\\=/P(O)(OR)$_2$ | 85 |
| 10 | cyclohexenyl–≡ | cyclohexenyl–\\=/P(O)(OR)$_2$ | 92 |
| 11 | ≡—(CH$_2$)$_5$—≡ | (RO)$_2$(O)P\\=/(CH$_2$)$_5$\\=/P(O)(OR)$_2$ | 89 |
| 12 | ≡—C$_6$H$_4$—≡ | (RO)$_2$(O)P\\=/C$_6$H$_4$\\=/P(O)(OR)$_2$ | 87 |
| 13 | thienyl–≡ | thienyl–\\=/P(O)(OR)$_2$ | 84 |

TABLE 1-continued

| Example | Acetylene | Product* | Yield (%) |
|---|---|---|---|
| 14 | Me₃Si—≡≡ | Me₃Si\ /<br>  /=\<br>     P(O)(OR)₂ | 90 |
| 15 | n-Pr—≡≡≡—n-Pr | n-Pr\ /n-Pr<br>    \=/<br>     P(O)(OR)₂ | 65 |

*(OR)₂ = 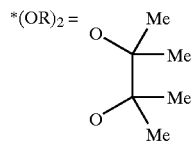

The above compounds are novel substances not described in literatures and have the following spectral data.

Product of Example 5

$^1$H-NMR (500 MHz, CDCl$_3$): δ 6.90 (ddt, 1H, J=6.7, 17.1 Hz, J$_{HP}$=23.1 Hz), 5.53 (dd, 1H, J=17.1 Hz, J$_{HP}$=23.8 Hz), 2.16–2.31 (m, 2H), 1.45 (s, 6H), 1.35 (s, 6H) 1.21–1.45 (m, 8H), 0.87 (t, 3H, J=6.7 Hz) $^{13}$C NMR (125.4 MHz, CDCl$_3$): δ 156.4, 117.1 (J$_{CP}$=183.1 Hz), 87.8, 34.2 (J$_{CP}$=21.7 Hz), 31.6, 28.8, 27.7, 24.7, 24.1 (J$_{CP}$=4.2 Hz), 22.5(J$_{CP}$=5.2 Hz), 14.0 $^{31}$P NMR (201.9 MHz, CDCl$_3$): δ 29.4 IR (liquid film): 2988, 2862, 1626, 1460, 1377, 1267, 1141, 965, 930, 872 cm$^{-1}$ HRMS as C$_{14}$H$_{27}$O$_3$P: calculated: 274.1698. measured: 274.1713.

| Elementary analysis: | |
|---|---|
| calculated: | C, 61.29; H, 9.92 |
| measured: | C, 60.86; H, 9.92 |

Product of Example 6

$^1$H-NMR (500 MHz, CDCl$_3$): δ 6.88 (dd, 1H, J=17.0 Hz, J$_{HP}$=24.0 Hz), 5.41 (dd, 1H, J=17.0 Hz, J$_{HP}$=22.8 Hz), 1.45 (s, 6H), 1.34(s, 6H), 1.03 (s, 9H) $^{13}$C NMR (125.4 MHz, CDCl$_3$): (165.5, 112.1 (J$_{CP}$=184.1 Hz), 87.9, 35.0 (J$_{CP}$=19.7 Hz), 28.3, 24.6(J$_{CP}$=4.2 Hz), 24.1(J$_{CP}$=5.2 Hz) 31P NMR (201.9 MHz, CDCl$_3$): (30.8 IR (KBr): 2958, 2870, 1620, 1464, 1381, 1247, 1172, 1139, 1015, 915, 874, 833 cm−1 HRMS as C$_{12}$H$_{23}$O$_3$P: calculated: 246.1385. measured: 246.1413.

| Elementary analysis: | |
|---|---|
| calculated: | C, 58.52; H, 9.41 |
| measured: | C, 58.85; H, 9.45 |

Product of Example 7

$^1$H-NMR (500 MHz, CDCl$_3$): δ 6.88 (ddt, 1H, J=7.0, 16.8 Hz, J$_{HP}$=22.8 Hz), 5.53 (ddt, 1H, J=1.6 16.8 Hz, J$_{HP}$=22.8 Hz), 3.52 (t, 2H, J=6.4 Hz), 2.37–2.42 (m, 2H), 1.89–1.95 (m, 2H), 1.49 (s, 6H), 1.35 (s, 6H) $^{13}$C-NMR (125.4 MHz, CDCl$_3$): δ 154.0, 118.8 (J$_{CP}$=183.1 Hz), 88.1, 44.0, 31.2 (J$_{CP}$=22.8 Hz), 30.5, 24.7 (J$_{CP}$=4.1 Hz), 24.1(J$_{CP}$=5.2 Hz) $^{31}$P NMR (201 .9 MHz, CDCl$_3$): δ 28.7 IR (liquid film): 2988, 1628, 1448, 1400, 1379, 1251, 1137, 963, 932, 882, 845, 818 cm$^{31\ 1}$ HRMS as C$_{11}$H$_{20}$ClO$_3$P: calculated: 266.0839. measured: 266.0861.

| Elementary analysis: | |
|---|---|
| calculated: | C, 49.54; H, 7.56 |
| measured: | C, 49.97; H, 7.68.5 |

Product of Example 8

$^1$H-NMR (500 MHz, CDCl$_3$): δ 6.82 (ddt, 1H, J=6.7, 16.8 Hz, J$_{HP}$=23.0 Hz), 5.53 (dd, 1H, J=16.8 Hz, J$_{HP}$=22.2 Hz), 2.34–2.40 (m, 4H), 1.78–1.84 (m, 2H), 1.47 (s, 6H), 1.34 (s, 6H) $^{13}$C NMR (125.4 MHz, CDCl$_3$): δ 152.8, 119.5 (J$_{CP}$=183.1 Hz), 119.0, 88.2, 32.6 (J$_{CP}$=23.8 Hz), 24.6 (J$_{CP}$=4.1 Hz), 24.1(J$_{CP}$=5.2 Hz), 23.5, 16.6 $^{31}$P NMR (201.9 MHz, CDCl$_3$): δ 28.1 IR (KBr): 2992, 2946, 2240, 1628, 1460, 1398, 1377, 1267, 1143, 1017, 965, 932, 870, 841, 814, 799 cm$^{-1}$ HRMS as C$_{12}$H$_{20}$NO$_3$P: calculated: 257.1181. measured: 257.1180.

| Elementary analysis: | |
|---|---|
| calculated: | C, 56.02; H, 7.84; N, 5.44 |
| measured: | C, 56.59; H, 7.85; N, 5.31 |

Product of Example 9

$^1$H-NMR (500 MHz, CDCl$_3$): δ 6.92 (ddd, 1H, J=3.4, 16.8 Hz, J$_{HP}$=23.5 Hz), 5.53 (ddd, 1H, J=2.2, 16.8 Hz, J$_{HP}$=23.2 Hz), 2.38 (bs, 1H), 1.47 (s, 6H), 1.34 (s, 6H), 1.32 (s, 6H) $^{13}$C NMR (125.4 MHz, CDCl$_3$): δ 161.7, 113.5 (J$_{CP}$=184.1 Hz), 71.5 (J$_{CP}$=20.7 Hz), 29.1, 24.6 (J$_{CP}$=4.2 Hz), 24.1(J$_{CP}$= 6.1 Hz) $^{31}$P NMR (201.9 MHz, CDCl$_3$): δ 30.4 IR (KBr): 3342, 2980, 1624, 1460, 1398, 1249, 1133, 961, 938, 872, 810 cm$^{-1}$ HRMS as C$_{11}$H$_{22}$O$_4$P(M+1): calculated: 249.1256. measured: 249.1349.

| Elementary analysis: | |
|---|---|
| calculated: | C, 53.22; H, 8.53 |
| measured: | C, 53.65; H, 8.66 |

Product of Example 10

$^1$H-NMR (500 MHz, CDCl$_3$): δ 7.20 (dd, 1H, J=17.1 Hz, J$_{HP}$=23.2 Hz), 6.14 (bs, 1H), 5.53 (dd, 1H, J=17.1 Hz, J$_{HP}$=21.0 Hz), 2.03 (bs, 2H), 2.11 (bs, 2H), 1.58–1.68 (m, 4H), 1.50 (s, 6H), 1.36 (s, 6H) $^{13}$C NMR (125.4 MHz, CDCl$_3$): δ 154.2, 138.9, 135.2 (J$_{CP}$=22.8 Hz), 109.5 (J$_{CP}$=188.3 Hz), 87.8, 26.3, 24.7 (J$_{CP}$=4.1 Hz), 24.1 (J$_{CP}$=5.1 Hz), 23.9, 22.1 $^{31}$P NMR (201.9 MHz, CDCl$_3$): δ 31.9 IR (KBr): 2982, 2914, 1634, 1595, 1450, 1398, 1379, 1253, 1222, 1141, 1013, 953, 928, 874 cm$^{-1}$ HRMS as C$_{14}$H$_{23}$O$_3$P: calculated: 270.1385. measured: 270.1404.

| Elementary analysis: | |
|---|---|
| calculated: | C, 62.21; H, 8.58 |
| measured: | C, 61.90; H, 8.54 |

Product of Example 11

$^1$H-NMR (500 MHz, CDCl$_3$): δ 6.90 (ddt, 2H, J=6.7, 16.7 Hz, J$_{HP}$=22.8 Hz), 5.56 (dd, 1H, J=16.7 Hz, J$_{HP}$=23.8 Hz), 2.19–2.23 (m, 4H), 1.32–1.52 (m, 6H), 1.49 (s, 12H), 1.36 (s, 12H) $^{13}$C NMR (125.4 MHz, CDCl$_3$): δ 156.0, 117.4 (J$_{CP}$=183.1 Hz), 87.9, 34.1 (J$_{CP}$=22.8 Hz), 28.6, 27.5, 24.7 (J$_{CP}$=4.1 Hz), 24.1 (J$_{CP}$=5.2 Hz) $^{31}$P NMR (201.9 MHz, CDCl$_3$): δ 29.3 IR (liquid film): 2988, 2936, 2334, 1626, 1377, 1263, 1139, 963, 930, 872, 799 cm$^{-1}$ HRMS as C$_{21}$H$_{38}$O$_6$P$_2$: calculated: 448.2144. measured: 448.2176.

| Elementary analysis: | |
|---|---|
| calculated: | C, 56.24; H, 8.54 |
| measured: | C, 56.49; H, 8.43 |

Product of Example 12

$^1$H-NMR (500 MHz, CDCl$_3$): δ 7.61 (dd, 2H, J=17.4, Hz, J$_{HP}$=23.5 Hz), 7.35–7.49 (m, 5H), 6.13 (dd, 2H, J=17.4 Hz, J$_{HP}$=19.5 Hz), 1.54(s, 12H), 1.42 (s, 12H) $^{13}$C NMR (125.4 MHz, CDCl$_3$): δ 149.5, 135.2, 128.3, 115.7 (J$_{CP}$=187.2 Hz), 88.3, 24.7 (J$_{CP}$=3.1 Hz), 24.2 (J$_{CP}$=5.2 Hz) $^{31}$P NMR (201.9 MHz, CDCl$_3$): δ 29.4 IR (KBr): 2986, 1611, 1296, 1261, 1135, 963, 938, 882, 797 cm$^{-1}$

| Elementary analysis, HRMS as C$_{22}$H$_{32}$O$_6$P$_2$: | |
|---|---|
| calculated: | C, 58.15; H, 7.10 |
| measured: | C, 58.53; H, 7.27 |

Product of Example 13

$^1$H-NMR (500 MHz, CDCl$_3$): δ 7.70 (dd, 1H, J=17.0 Hz, J$_{HP}$=23.0 Hz), 7.01–7.36 (m, 3H), 5.84 (dd, 1H, J=17.0 Hz, J$_{HP}$=18.9 Hz), 1.52 (s, 6H), 1.40 (s, 6H) $^{13}$C NMR (125.4 MHz, CDCl$_3$): δ 143.2, 140.3 (J$_{CP}$=27.0 Hz), 130.8, 128.6, 128.1, 112.5 (J$_{CP}$=190.3 Hz), 88.2, 24.7 (J$_{CP}$=4.1 Hz), 24.2 (J$_{CP}$=6.2 Hz) $^{31}$P NMR (201.9 MHz, CDCl$_3$): δ 29.8 HRMS as C$_{12}$H$_{17}$O$_3$PS: calculated: 272.0636. measured: 272.0636.

| Elementary analysis: | |
|---|---|
| calculated: | C, 52.93; H, 6.29 |
| measured: | C, 52.77; H, 6.28 |

Product of Example 14

$^1$H-NMR (500 MHz, CDCl$_3$): δ 7.30 (dd, 1H, J=20.5 Hz, J$_{HP}$=35.7 Hz), 6.15 (dd, 1H, J=20.5 Hz, J$_{HP}$=30.2 Hz), 1.46 (s, 6H), 1.33 (s, 6H), 0.08 (s, 9H) $^{13}$C NMR (125.4 MHz, CDCl$_3$): δ 158.1, 132.0 (J$_{CP}$=168.6 Hz), 88.1, 24.7 (J$_{CP}$=4.1 Hz), 24.1 (J$_{CP}$=5.1 Hz), -2.1 $^{31}$P NMR (201.9 MHz, CDCl$_3$): δ 27.0 IR (KBr): 2958, 1700, 1506, 1379, 1255, 1139, 1011, 950, 870, 758 cm$^{-1}$ HRMS as C$_{11}$H$_{23}$O$_3$PSi: calculated: 262.1154. measured: 262.1096.

| Elementary analysis: | |
|---|---|
| calculated: | C, 50.36; H, 8.84 |
| measured: | C, 50.64; H, 8.89 |

Product of Example 15

$^1$H-NMR (500 MHz, CDCl$_3$): δ 6.40 (dt, 1H, J=7.3 Hz, J$_{HP}$=24.3 Hz), 2.25–2.32 (m, 2H), 2.10–2.15 (m, 2H), 1.42–1.56 (m, 4H), 1.50 (s, 6H), 1.32 (s, 6H), 0.92 (t, 6H, J=7.3 Hz) $^{13}$C NMR (125.4 MHz, CDCl$_3$): δ 144.8, 130.8 (J$_{CP}$=170.7 Hz), 87.8, 30.3 (J$_{CP}$=20.0 Hz), 29.6 (J$_{CP}$=12.4 Hz), 25.1(J$_{CP}$=4.2 Hz), 24.1 (J$_{CP}$=5.1 Hz), 22.5, 21.9, 14.1, 13.9 $^{31}$P NMR (201.9 MHz, CDCl$_3$): δ 33.3 IR (liquid film): 2964, 2876, 1620, 1460, 1377, 1263, 1139, 963, 928, 872, 804 cm$^{-1}$ Example 16

To 1 ml of tetrahydrofuran were added 1 mmol of HP(O)(OCMe$_2$-CMe$_2$O), 1 mmol of phenylacetylene and 3 mol % of RhCl(PPh$_3$)$_3$ as a catalyst, and the mixture was reacted at 23° C. for 48 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 97%.

Example 17

To 1 ml of dichloromethane were added 1 mmol of HP(O)(OCMe$_2$-CMe$_2$O), 1 mmol of phenylacetylene and 3 mol % of RhCl (PPh$_3$)$_3$ as a catalyst, and the mixture was reacted at 23° C. for 6 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 92%.

Example 18

To 1 ml of acetonitrile were added 1 mmol of HP(O)(OCMe$_2$-CMe$_2$O), 1 mmol of phenylacetylene and 3 mol % of RhCl(PPh$_3$)$_3$ as a catalyst, and the mixture was reacted at 23° C. for 48 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 91%.

Example 19

To 1 ml of acetone were added 1 mmol of HP(O)(OCMe$_2$-CMe$_2$O), 1 mmol of phenylacetylene and 3 mol % of RhCl(PPh$_3$)$_3$ as a catalyst, and the mixture was reacted at 23° C. for 4 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 98%.

Example 20

To 1 ml of acetone were added 1 mmol of HP(O)(OCMe$_2$-CMe$_2$O), 1 mmol of phenylacetylene and 3 mol % of RhBr(PPh$_3$)$_3$ as a catalyst, and the mixture was reacted at 23° C. for 5 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 99%.

Example 21

To 1 ml of acetone were added 1 mmol of HP(O)(OCMe$_2$-CMe$_2$O), 1 mmol of phenylacetylene and 3 mol % of RhBr(PPh$_3$)$_3$ as a catalyst, and the mixture was reacted at 23° C. for 5 hours in an atmosphere of nitrogen. The reaction mixture was concentrated and separated by liquid chromatography to isolate 2-[(E)-2-phenylethenyl]-4,4,5,5-tetramethyl-1,3,2-dioxaphospholan-2-oxide with a yield of 99%.

Examples 22–31

Example 20 was repeated in the same manner as described using various acetylene compounds to obtain phosphonic acid esters of the present invention. The results are summarized in Table 2.

TABLE 2

| Example | Acetylene | Product* | Yield (%) |
|---|---|---|---|
| 22 | n-C$_6$H$_{13}$—≡ | n-C$_6$H$_{13}$\\=/P(O)(OR)$_2$ | 95 |
| 23 | t-Bu—≡ | t-Bu\\=/P(O)(OR)$_2$ | 79 |
| 24 | Cl\\/\\≡ | Cl\\/\\/\\=/P(O)(OR)$_2$ | 89 |
| 25 | NC\\/\\≡ | NC\\/\\/\\=/P(O)(OR)$_2$ | 95 |
| 26 | HO-C(CH$_3$)$_2$-≡ | HO-C(CH$_3$)$_2$-CH=CH-P(O)(OR)$_2$ | 82 |
| 27 | cyclohexenyl-≡ | cyclohexenyl-CH=CH-P(O)(OR)$_2$ | 92 |
| 28 | ≡—(CH$_2$)$_5$—≡ | (RO)$_2$(O)P—CH=CH—(CH$_2$)$_5$—CH=CH—P(O)(OR)$_2$ | 93 |
| 29 | ≡—C$_6$H$_4$—≡ | (RO)$_2$(O)P—CH=CH—C$_6$H$_4$—CH=CH—P(O)(OR)$_2$ | 97 |

TABLE 2-continued

| Example | Acetylene | Product* | Yield (%) |
|---|---|---|---|
| 30 | (thiophene-C≡CH) | (thiophene-CH=CH-P(O)(OR)$_2$) | 46 |
| 31 | Me$_3$Si—≡ | Me$_3$Si-CH=CH-P(O)(OR)$_2$ | 76 |

*(OR)$_2$ = 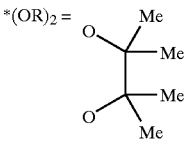

Example 32

To 1 ml of acetone were added 1 mmol of HP(O)(OCMe$_2$-CMe$_2$O) and 3 mol % of RhBr(PPh$_3$)$_3$. This was reacted in the atmosphere of acetylene gas at atmospheric pressure at 23° C. for 20 hours. The reaction mixture was concentrated and separated by liquid chromatography to isolate 2-ethenyl-4,4,5,5-tetramethyl-1,3,2-dioxaphosphoran-2-oxide with a yield of 81%. This compound is a novel substance not described in literatures and has the following spectral data.

$^1$H-NMR (500 MHz, CDCl$_3$): δ 6.41 (ddd, 1H, J=2.1, 18.6 Hz, J$_{HP}$=26.2 Hz), 6.17 (ddd, 1H, J=2.1, 12.9 Hz, J$_{HP}$=52.8 Hz), 6.04 (ddd, 1H, J=12.9, 18.6 Hz, J$_{HP}$=24.7 Hz), 1.51 (s, 6H), 1.36 (s, 6H) $^{13}$C-NMR (125.4 MHz, CDCl$_3$): δ 137.2, 126.5 (J$_{CP}$=180.0 Hz), 88.3, 24.7 (J$_{CP}$=5.2 Hz), 24.1 (J$_{CP}$=3.1 Hz) $^{31}$P-NMR (201.9 MHz, CDCl$_3$): δ 28.0 IR (liquid film): 2992, 1398, 1379, 1137, 1021, 963, 936 cm$^{-1}$ HRMS as C$_8$H$_{15}$O$_3$P: calculated: 190.0759. measured: 190.0779.

The alkenylphosphonic acid ester represented by the above general formula (I) and the alkenyldiphosphonic acid esters represented by the above general formulas (IV) and (V) according to the present invention are novel compounds with a cyclic phosphonic acid ester structure which are not described in any literature. The novel compounds are useful as an agent for forming carbon-carbon bonds, for example, as an intermediate compounds for the production of physiologically active substances of medicaments or agricultural chemicals. Because of the cyclic structure, the novel compounds have considerably higher reaction activity as compared with similar non-cyclic compounds. Thus, the cyclic alkenylphosphonic acid esters are expected to allow chemical conversion, which would otherwise be difficult or impossible to perform, to proceed efficiently under milder conditions.

The method according to the present invention permits the synthesis of the above alkenylphosphonic acid esters in a simple, safe and efficient manner by merely reacting acetylenes with cyclic secondary phosphonic acid esters. The separation and purification of the product is also very easy.

Therefore, the present invention provides a great industrial effect.

What is claimed is:

1. An alkenylphosphonic acid ester compound of the following general formula (I):

$$R^1CH=CR^2[P(O)(OCR^3R^4CR^5R^6O)] \qquad (I)$$

wherein $R^1$ and $R^2$ each stand for a hydrogen atom, an alkyl group, a cycloalkyl group, an aryl group, an aralkyl group, a heteroaryl group, an alkenyl group, an alkoxy group, an aryloxy group or a silyl group, provided that $R^1$ does not stand for a hydrogen atom or a methyl group, and $R^3$, $R^4$, $R^5$ and $R^6$ each stand for a hydrogen atom, an alkyl group, a cycloalkyl group, an aralkyl group or an aryl group.

2. A process for the preparation of an alkenylphosphonic acid ester compound, comprising reacting an acetylene compound of the following formula (II):

$$R^1C{\equiv}CR^2 \qquad (II)$$

wherein $R^1$ and $R^2$ each stand for a hydrogen atom, an alkyl group, a cycloalkyl group, an aryl group, an aralkyl group, a heteroaryl group, an alkenyl group, an alkoxy group, an aryloxy group or a silyl group, with a cyclic secondary phosphonic acid ester of the following formula (III):

$$HP(O)(OCR^3R^4CR^5R^6O) \qquad (III)$$

wherein $R^3$, $R^4$, $R^5$ and $R^6$ each stand for a hydrogen atom, an alkyl group, a cycloalkyl group, an aralkyl group or an aryl group, in the presence of a catalyst of a metal of Group 9 of the Periodic Table to obtain an alkenylphosphonic acid ester compound of the following formula (I):

$$R^1CH=CR^2[P(O)(OC\ R^3R^4CR^5R^6O)] \qquad (I)$$

wherein $R^1$, $R^2$, $R^3$, $R^4$, $R^5$ and $R^6$ have the same meaning as above.

3. A process for the preparation of an alkenylphosphonic acid ester compound as claimed in claim 2, wherein said catalyst is a rhodium catalyst.

4. A process for the preparation of an alkenylphosphonic acid ester compound as claimed in claim 2, wherein said reacting is in the presence of a polar solvent.

5. A process for the preparation of an alkenylphosphonic acid ester compound as claimed in claim 3, wherein said reacting is in the presence of a polar solvent.

6. A process for the preparation of an alkenylphosphonic acid ester compound as claimed in claim 2, wherein said catalyst comprises the metal and a tertiary phosphine or tertiary phosphite ligand.

7. A process for the preparation of an alkenylphosphonic acid ester compound as claimed in claim 3, wherein said catalyst comprises the metal and a tertiary phosphine or tertiary phosphite ligand.

8. A process for the preparation of an alkenylphosphonic acid ester compound as claimed in claim 4, wherein said catalyst comprises the metal and a tertiary phosphine or tertiary phosphite ligand.

9. A process for the preparation of an alkenylphosphonic acid ester compound as claimed in claim 5, wherein said catalyst comprises the metal and a tertiary phosphine or tertiary phosphite ligand.

10. A process for the preparation of an alkenylphosphonic acid ester compound as claimed in claim 2, wherein the metal is selected from the group consisting of cobalt, rhodium and iridium.

11. A process for the preparation of an alkenylphosphonic acid ester compound as claimed in claim 6, wherein the metal is selected from the group consisting of cobalt, rhodium and iridium.

12. A process for the preparation of an alkenylphosphonic acid ester compound as claimed in claim 7, wherein the metal is selected from the group consisting of cobalt, rhodium and iridium.

13. A process for the preparation of an alkenylphosphonic acid ester compound as claimed in claim 8, wherein the metal is selected from the group consisting of cobalt, rhodium and iridium.

14. A process for the preparation of an alkenylphosphonic acid ester compound as claimed in claim 9, wherein the metal is selected from the group consisting of cobalt, rhodium and iridium.

15. An alkenylphosphonic acid ester compound according to claim 1 wherein $R^1$ and $R^2$ are each selected from the group consisting of hydrogen, alkyl, cycloalkyl, aryl, aralkyl, heteroaryl alkenyl, aryloxy and silyl.

* * * * *